(12) United States Patent
Schmidt et al.

(10) Patent No.: US 6,620,931 B2
(45) Date of Patent: Sep. 16, 2003

(54) PROCESS FOR PREPARING NEW CRYSTAL POLYMORPHS OF A METHYL-SUBSTITUTED BENZIMIDAZOLONE-DIOXAZINE PIGMENT

(75) Inventors: Martin U. Schmidt, Frankfurt am Main (DE); Peter Kempter, Bad Soden (DE); Roland Born, Village-Neuf (FR)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/047,829

(22) Filed: Oct. 22, 2001

(65) Prior Publication Data

US 2002/0123626 A1 Sep. 5, 2002

(30) Foreign Application Priority Data

Oct. 21, 2000 (DE) .......................................... 100 52 221

(51) Int. Cl.⁷ ............................................. C07D 498/22

(52) U.S. Cl. ................. 544/74; 8/506; 8/648

(58) Field of Search .................... 544/99, 74; 8/506, 8/648

(56) References Cited

U.S. PATENT DOCUMENTS

| | | | |
|---|---|---|---|
| 3,472,844 A | 10/1969 | Fry et al. ................. | 260/246 |
| 4,481,358 A | 11/1984 | Sakaguchi et al. ............ | 544/99 |
| 5,565,563 A | * 10/1996 | Kaul et al. ..................... | 544/74 |
| 6,214,989 B1 | * 4/2001 | Kaul et al. ..................... | 544/74 |

FOREIGN PATENT DOCUMENTS

| | | |
|---|---|---|
| DE | 1 619 389 | 6/1971 |
| DE | 32 11 607 | 10/1982 |
| DE | 44 42 291 | 6/1995 |
| EP | 0 911 337 | 4/1999 |

OTHER PUBLICATIONS

EPO search report for application No. 01124076, mail date Jan. 18, 2002.
U.S. patent application, Ser. No. 10/001,777, filed Oct. 24, 2001.

* cited by examiner

Primary Examiner—Mukund J. Shah
Assistant Examiner—Thomas McKenzie
(74) Attorney, Agent, or Firm—Anthony A. Bisulca

(57) ABSTRACT

Process for phase conversion of a methyl-substituted, benzimidazolone-fused dioxazine pigment of composition $C_{22}H_{12}Cl_2N_6O_4$ having the formula (1)

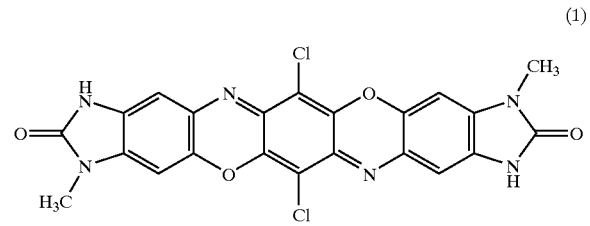

(1)

or of an isomer or tautomer thereof, which comprises treating the pigment of formula (1) with certain organic solvents.

In the course of this phase conversion, 4 novel crystal polymorphs are formed which are called phases II, IV, V and VI and are characterized by means of their X-ray powder diagrams.

The novel polymorphs are of low solubility and feature good fastness properties and violet colorations.

The novel crystal polymorphs are suitable for pigmenting coating materials, plastics, printing inks, aqueous or solvent-based pigment preparations, electrophotographic toners and developers, powder coating materials, inks, preferably inkjet inks, and color filters, and for coloring seed.

13 Claims, No Drawings

PROCESS FOR PREPARING NEW CRYSTAL POLYMORPHS OF A METHYL-SUBSTITUTED BENZIMIDAZOLONE-DIOXAZINE PIGMENT

BACKGROUND OF THE INVENTION

The invention relates to novel crystal polymorphs of methyl-substituted benzimidazolone-dioxazine pigment of the formula (1)

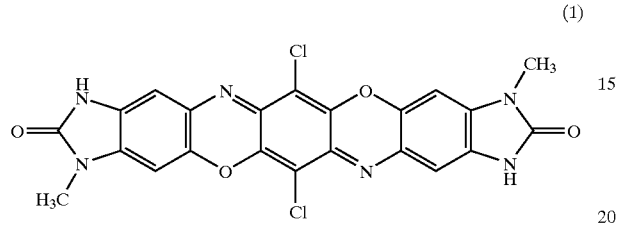

(1)

The compound of the formula (1) was first described in DE-A-44 42 291. An alternative synthesis of analogous compounds is described in EP-A-0 911 337.

The majority of organic pigments exist in a plurality of different crystal forms, also called polymorphs. Crystal polymorphs have the same chemical composition but a different arrangement of the building blocks (molecules) in the crystal. The crystal structure determines the chemical and physical properties: consequently, the individual crystal polymorphs frequently differ in rheology, color, and other coloristic properties. The different crystal polymorphs may be identified by means of X-ray powder diffractometry.

At the present time there are two known crystal polymorphs of the dioxazine pigment of the formula (1), which are referred to below as phase I and phase III and are distinguished by the following characteristic lines in the X-ray powder diagram (Cu—$K_\alpha$ radiation, double the Bragg angle $2\Theta$ in degrees, interplanar spacings d in $\text{Å}^{-1}$):

| $2\Theta$ | d | rel. intensity |
|---|---|---|
| Phase I: | | |
| 5.00 | 17.68 | 28 |
| 6.08 | 14.53 | 14 (broad) |
| 10.58 | 8.35 | 24 |
| 10.98 | 8.05 | 24 |
| 20.38 | 4.35 | 11 (broad) |
| 22.20 | 4.00 | 10 (broad) |
| 25.18 | 3.53 | 11 (broad) |
| 27.16 | 3.28 | 100 |
| Phase III: | | |
| 5.22 | 16.92 | 23 broad |
| 6.18 | 14.30 | 24 broad |
| 10.92 | 8.09 | 17 broad |
| 11.81 | 7.49 | 30 broad |
| 12.34 | 7.17 | 35 broad |
| 14.32 | 6.18 | 13 broad |
| 17.07 | 5.19 | 10 broad |
| 20.31 | 4.37 | 12 broad |
| 23.16 | 3.84 | 14 broad |
| 25.64 | 3.47 | 18 broad |
| 26.99 | 3.30 | 100 |

The line positions noted as being "broad" are given to an accuracy of ±0.4°, all other line positions to an accuracy of ±0.2°.

Phases I and III develop during the synthesis of the dioxazine pigment of the formula (1) in accordance with DE-A-44 42 291 or EP-A-0 911 337.

SUMMARY OF THE INVENTION

It has now surprisingly been found that novel crystal polymorphs are formed if the pigment of the formula (1) is treated with certain organic solvents. This is all the more surprising since treating the analogous pigment of the formula (2) with organic solvents is not accompanied by the development of any new crystal phases.

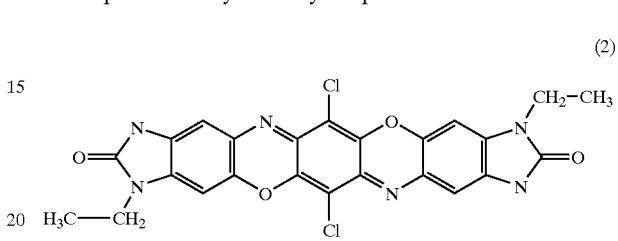

(2)

DESCRIPTION OF THE PREFERRED EMBODIMENTS

The novel crystal polymorphs of the dioxazine pigment of the formula (1) are referred to as phases II, IV, V and VI.

They are distinguished by the following characteristic lines (Cu—$K_\alpha$ radiation, $2\Theta$ in degrees, d in $\text{Å}^{-1}$):

| $2\Theta$ | d | rel. intensity |
|---|---|---|
| Phase II: | | |
| 6.64 | 13.29 | 21 |
| 11.05 | 8.00 | 8 |
| 12.49 | 7.08 | 46 |
| 13.41 | 6.60 | 6 |
| 14.60 | 6.06 | 10 |
| 17.08 | 5.19 | 7 |
| 19.87 | 4.46 | 7 |
| 20.93 | 4.24 | 4 |
| 22.24 | 3.99 | 4 |
| 23.35 | 3.81 | 8 |
| 25.36 | 3.51 | 11 |
| 26.90 | 3.31 | 100 |
| 29.06 | 3.07 | 5 |
| 30.48 | 2.93 | 8 |
| 32.11 | 2.79 | 8 |
| 33.17 | 2.70 | 4 |
| Phase IV: | | |
| 6.51 | 13.56 | 96 |
| 11.15 | 7.93 | 100 |
| 13.09 | 6.76 | 24 |
| 14.49 | 6.11 | 41 |
| 19.63 | 4.52 | 27 |
| 22.40 | 3.97 | 28 |
| 23.67 | 3.76 | 23 |
| 25.34 | 3.51 | 23 |
| 27.47 | 3.24 | 95 |
| 29.49 | 3.03 | 18 |
| Phase V: | | |
| 5.04 | 17.51 | 13 |
| 7.53 | 11.73 | 12 |
| 7.95 | 11.12 | 13 |
| 9.38 | 9.42 | 15 |
| 10.32 | 8.57 | 14 |
| 10.94 | 8.08 | 15 |
| 12.33 | 7.17 | 10 |
| 13.49 | 6.56 | 9 |

-continued

| 2Θ | d | rel. intensity |
|---|---|---|
| 14.94 | 5.92 | 8 |
| 16.51 | 5.36 | 9 |
| 17.04 | 5.20 | 8 |
| 18.27 | 4.85 | 9 |
| 19.75 | 4.49 | 9 |
| 21.08 | 4.21 | 8 |
| 22.26 | 3.99 | 9 |
| 24.12 | 3.69 | 7 |
| 25.17 | 3.53 | 7 |
| 27.25 | 3.27 | 100 |
| 30.44 | 2.93 | 6 |
| Phase VI: | | |
| 6.83 | 12.94 | 69 |
| 9.36 | 9.45 | 32 |
| 9.88 | 8.95 | 23 |
| 13.69 | 6.46 | 36 |
| 14.29 | 6.19 | 20 |
| 14.87 | 5.95 | 24 |
| 15.44 | 5.74 | 39 |
| 15.89 | 5.57 | 23 |
| 18.22 | 4.87 | 35 |
| 18.67 | 4.75 | 44 |
| 19.68 | 4.51 | 20 |
| 19.81 | 4.48 | 21 |
| 20.32 | 4.37 | 30 |
| 21.09 | 4.21 | 26 |
| 21.49 | 4.13 | 31 |
| 21.77 | 4.08 | 30 |
| 22.41 | 3.96 | 23 |
| 22.58 | 3.93 | 23 |
| 23.52 | 3.78 | 24 |
| 24.69 | 3.60 | 24 |
| 25.07 | 3.55 | 19 |
| 26.56 | 3.35 | 100 |
| 28.44 | 3.14 | 45 |
| 29.21 | 3.05 | 16 |
| 29.99 | 2.98 | 17 |
| 30.51 | 2.93 | 15 |

All of the line positions of phases II, IV, V and VI are given to an accuracy of ±0.2°.

The abovementioned phases are of extremely low solubility and feature good fastness properties and violet colorations.

The different phases exhibit different coloristic properties.

In the solid state, the compound of the formula (1) may also be present in a different tautomeric and/or isomeric form.

The invention provides a process for the phase conversion of a compound of the formula (1)

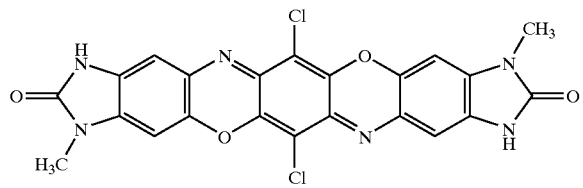

(1)

or of an isomer, tautomer or isomeric tautomer thereof, which comprises causing to act on the compound of the formula (1) an organic solvent selected from the group consisting of N-methylpyrrolidone, $C_1$–$C_{20}$-alcohol, e.g. methanol, ethanol, n-propanol, iso-propanol, n-, iso- or tert-butanol, 1,2,4-trichlorobenzene, dichloroacetic acid and trifluoroacetic acid, or a mixture of said solvents, or a mixture of 1,2-dichlorobenzene and trifluoroacetic acid, at a temperature of between 0 and 250° C., preferably between 20 and 210° C.

The process of the invention is appropriately conducted such that the compound of the formula (1) is suspended or fully or partly dissolved in the respective organic solvent and the mixture is held at the stated temperature for from 10 minutes to 48 hours, preferably from 30 minutes to 24 hours.

The starting material for preparing the phases of the invention is preferably the compound of the formula (1) in phase I, although it is also possible in each case to use the measures described to convert one or more of the novel crystal phases into one of the other said crystal phases.

Phase II is obtained, for example, by heating the pigment of the formula (1) to boiling with N-methylpyrrolidone.

Phase IV is obtained, for example, by dissolving the pigment of the formula (1) in trifluoroacetic acid and reprecipitating it by adding acetic acid.

Phase V is obtained, for example, by dissolving the pigment of the formula (1) in a mixture of trifluoroacetic acid and o-dichlorobenzene, preferably in a ratio of from 1:10 to 10:1, in particular from 1:2 to 2:1, and reprecipitating the pigment by evaporating the trifluoroacetic acid.

Phase VI is obtained, for example, by dissolving the pigment of the formula (1) in trifluoroacetic acid and reprecipitating the pigment by evaporating the trifluoroacetic acid.

Depending on the purity of the reactants, the concentrations, the temperatures and temperature programs employed, any aftertreatment, the pressure, the presence of impurities or additives, and the presence of seed crystals, it is possible for pure phase II, IV, V or VI, or a mixture comprising two or more of these phases to be formed.

The present invention therefore additionally provides a mixture of pigments of the formula (1) comprising at least 10%, preferably at least 25%, in particular at least 50%, with particular preference at least 75% and with very particular preference at least 90% of phase II, of phase IV, of phase V, of phase VI, or a mixture of two, three or four of these phases.

Depending on the desired field of application, it may be sensible to subject the resulting pigment to mechanical fine division. The fine division may be carried out by wet or dry grinding or by kneading. Grinding and/or kneading may be followed by treatment with a solvent, with water, or with a solvent/water mixture.

To facilitate the change of polymorph, to stabilize the polymorphs of the invention, to enhance the coloristic properties, and to achieve particular coloristic effects it is possible at any point in the process to add pigment dispersants, surface-active agents, defoamers, extenders or other additives. It is also possible to use mixtures of these additives. The additives may be added all at once or in two or more portions. The additives may be added at any point in the synthesis or in the various aftertreatments, or following the aftertreatments. The point in time that is best suited must be determined beforehand by means of rangefinding tests.

The dioxazine pigment of the formula (1) in phase II, IV, V or VI, or a mixture comprising these phases, is suitable for pigmenting coating materials, plastics, and cosmetics, for producing printing inks, for printing paper and textiles, for example, and pigment preparations, for the pulp dyeing of paper, and for coloring seed.

The abovementioned phases and phase mixtures of the dioxazine pigment of the formula (1) are suitable for use as colorants in electrophotographic toners and developers, such as one- or two-component powder toners (also called one- or two-component developers), for example, magnetic toners, liquid toners, latex toners, addition-polymerization toners, and specialty toners.

Typical toner binders are addition-polymerization, polyaddition, and polycondensation resins, such as styrene, styrene acrylate, styrene butadiene, acrylate, polyester, and phenol-epoxy resins, polysulfones, polyurethanes, individually or in combination, and also polyethylene and polypropylene, which may contain further ingredients, such as charge control agents, waxes or flow aids, or may be subsequently modified with these additives.

The abovementioned phases and phase mixtures of the dioxazine pigment of the formula (1) are also suitable for use as colorants in powders and powder coating materials, especially in triboelectrically or electrokinetically sprayable powder coating materials that are used to coat the surfaces of articles comprising, for example, metal, wood, plastic, glass, ceramic, concrete, textile material, paper or rubber.

Powder coating resins that are employed typically comprise epoxy resins, carboxyl- and hydroxyl-containing polyester resins, polyurethane resins, and acrylic resins, together with customary curing agents. Resin combinations are also employed. For example, epoxy resins are frequently used in combination with carboxyl- and hydroxyl-containing polyester resins. Examples of typical curing components (depending on the resin system) are acid anhydrides, imidazoles, and also dicyandiamide and its derivatives, blocked isocyanates, bisacylurethanes, phenolic and melamine resins, triglycidyl isocyanurates, oxazolines, and dicarboxylic acids.

Furthermore, the abovementioned phases and phase mixtures are suitable for use as colorants in inks, preferably inkjet inks, such as those on an aqueous or nonaqueous basis, for example; in microemulsion inks; and in those inks which operate in accordance with the hot-melt process.

Inkjet inks generally contain a total of from 0.5 to 15% by weight, preferably from 1.5 to 8% by weight (calculated on a dry basis), of one or more of the compounds of the invention.

Microemulsion inks are based on organic solvents, water and, if desired, an additional hydrotropic substance (interface mediator). Microemulsion inks contain from 0.5 to 15% by weight, preferably from 1.5 to 8% by weight, of one or more of the compounds of the invention, from 5 to 99% by weight of water, and from 0.5 to 94.5% by weight of organic solvent and/or hydrotropic compound.

Solvent-based inkjet inks contain preferably from 0.5 to 15% by weight of one or more compounds of the invention and from 85 to 99.5% by weight of organic solvent and/or hydrotropic compounds.

Hot-melt inks are based generally on waxes, fatty acids, fatty alcohols or sulfonamides which are solid at room temperature and liquefy on heating, the preferred melting range being between about 60° C and about 140° C. Hot-melt inkjet inks consist substantially, for example, of from 20 to 90% by weight of wax and from 1 to 10% by weight of one or more of the compounds of the invention. It is also possible for from 0 to 20% by weight of an additional polymer (as "dye dissolver"), from 0 to 5% by weight of dispersing aids, from 0 to 20% by weight of viscosity modifiers, from 0 to 20% by weight of plasticizers, from 0 to 10% by weight of tack additive, from 0 to 10% by weight of transparency stabilizer (which prevents, for example, crystallization of the waxes), and from 0 to 2% by weight of antioxidant to be present. Typical additives and auxiliaries are described, for example, in U.S. Pat. No. 5,560,760.

In addition, the compounds of the invention are also suitable for use as colorants for color filters, both for additive and for subtractive color generation, and for "electronic inks".

In the examples below, parts and percentages are by weight. The crystal polymorph of the products obtained is determined by means of X-ray powder diffractometry.

EXAMPLES

Comparative Example

The pigment of the formula (1) is synthesized in analogy to the method described in EP-A-0 911 337, Example 3. This gives the pigment of the formula (1) in phase I.

Example 1

Preparation of phase II by heating in NMP 40 parts of pigment of the formula (1) which is present in phase I are heated in 400 parts of N-methyl-2-pyrrolidone at 203° C. for 18 hours, cooled to room temperature, filtered and then washed with water. This gives 38.1 parts of pigment of the formula (1) in phase II.

Example 2

Preparation of phase IV by recrystallization from trifluoroacetic acid/glacial acetic acid 35 parts of pigment of the formula (1) which is present in phase I are dissolved in 740 parts of trifluoroacetic acid and the solution is stirred at room temperature in 4200 parts of acetic acid. The mixture is heated to boiling for 5 minutes and the precipitate is filtered off, washed with acetone and dried. This gives pigment of the formula (1) in phase IV.

Example 3

Preparation of phase V by recrystallization from trifluoroacetic acid/dichlorobenzene 1 part of pigment of the formula (1) which is present in phase I is dissolved in 25 parts of a mixture of equal parts of o-dichlorobenzene and trifluoroacetic acid at room temperature and the trifluoroacetic acid is left to evaporate slowly at this temperature. This gives pigment of the formula (1) in phase V.

Example 4

Preparation of phase VI by recrystallization from trifluoroacetic acid. Pigment of the formula (I) which is present in phase I is dissolved at room temperature in trifluoroacetic acid and the trifluoroacetic acid is slowly evaporated at room temperature. This gives pigment of the formula (1) in phase VI.

Use Examples

To evaluate the properties in the coating sector of the pigment phases prepared in accordance with the invention, a selection was made from among the large number of known varnishes of an alkyd-melamine resin varnish (AM) containing aromatics and based on a medium-oil alkyd resin and on a butanol-etherified melamine resin.

Use Example 1

Application of the phase II pigment from Example 1 in AM varnish gives a strongly colored, clean, violet coating which is cleaner and more strongly colored than that of phase I and substantially bluer than that of phase III.

Use Example 2

Application of the phase IV pigment from Example 2 in AM varnish gives a violet coating which is substantially bluer than that of phase I or III and more strongly colored than that of phase I.

Use Example 3

Application of the phase V pigment from Example 3 in AM varnish gives a clean and violet coating which is more hiding and cleaner than that of phase I.

Use Example 4

Application of the phase VI pigment from Example 4 in AM varnish gives a clean and violet coating which is more hiding and cleaner than that of phase I.

What is claimed is:

1. A dioxazine pigment of the formula (1)

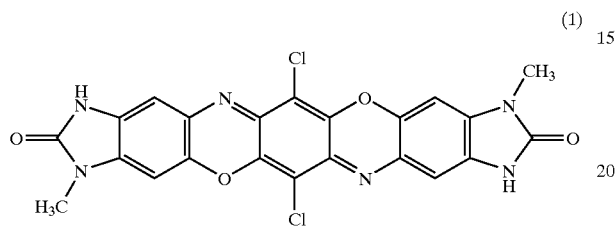

(1)

or a tautomer thereof, characterized by the following characteristic reflections in the X-ray powder diagram, measured with Cu—$K_\alpha$ radiation (2Θ in degrees, d in Å$^{-1}$):

| 2Θ | d | rel. intensity |
|---|---|---|
| Phase II: | | |
| 6.64 | 13.29 | 21 |
| 11.05 | 8.00 | 8 |
| 12.49 | 7.08 | 46 |
| 13.41 | 6.60 | 6 |
| 14.60 | 6.06 | 10 |
| 17.08 | 5.19 | 7 |
| 19.87 | 4.46 | 7 |
| 20.93 | 4.24 | 4 |
| 22.24 | 3.99 | 4 |
| 23.35 | 3.81 | 8 |
| 25.36 | 3.51 | 11 |
| 26.90 | 3.31 | 100 |
| 29.06 | 3.07 | 5 |
| 30.48 | 2.93 | 8 |
| 32.11 | 2.79 | 8 |
| 33.17 | 2.70 | 4 |
| or | | |
| Phase IV: | | |
| 6.51 | 13.56 | 96 |
| 11.15 | 7.93 | 100 |
| 13.09 | 6.76 | 24 |
| 14.49 | 6.11 | 41 |
| 19.63 | 4.52 | 27 |
| 22.40 | 3.97 | 28 |
| 23.67 | 3.76 | 23 |
| 25.34 | 3.51 | 23 |
| 27.47 | 3.24 | 95 |
| 29.49 | 3.03 | 18 |
| or | | |
| Phase V: | | |
| 5.04 | 17.51 | 13 |
| 7.53 | 11.73 | 12 |
| 7.95 | 11.12 | 13 |
| 9.38 | 9.42 | 15 |
| 10.32 | 8.57 | 14 |
| 10.94 | 8.08 | 15 |
| 12.33 | 7.17 | 10 |
| 13.49 | 6.56 | 9 |
| 14.94 | 5.92 | 8 |
| 16.51 | 5.36 | 9 |

-continued

| 2Θ | d | rel. intensity |
|---|---|---|
| 17.04 | 5.20 | 8 |
| 18.27 | 4.85 | 9 |
| 19.75 | 4.49 | 9 |
| 21.08 | 4.21 | 8 |
| 22.26 | 3.99 | 9 |
| 24.12 | 3.69 | 7 |
| 25.17 | 3.53 | 7 |
| 27.25 | 3.27 | 100 |
| 30.44 | 2.93 | 6 |
| or | | |
| Phase VI: | | |
| 6.83 | 12.94 | 69 |
| 9.36 | 9.45 | 32 |
| 9.88 | 8.95 | 23 |
| 13.69 | 6.46 | 36 |
| 14.29 | 6.19 | 20 |
| 14.87 | 5.95 | 24 |
| 15.44 | 5.74 | 39 |
| 15.89 | 5.57 | 23 |
| 18.22 | 4.87 | 35 |
| 18.67 | 4.75 | 44 |
| 19.68 | 4.51 | 20 |
| 19.81 | 4.48 | 21 |
| 20.32 | 4.37 | 30 |
| 21.09 | 4.21 | 26 |
| 21.49 | 4.13 | 31 |
| 21.77 | 4.08 | 30 |
| 22.41 | 3.96 | 23 |
| 22.58 | 3.93 | 23 |
| 23.52 | 3.78 | 24 |
| 24.69 | 3.60 | 24 |
| 25.07 | 3.55 | 19 |
| 26.56 | 3.35 | 100 |
| 28.44 | 3.14 | 45 |
| 29.21 | 3.05 | 16 |
| 29.99 | 2.98 | 17 |
| 30.51 | 2.93 | 15. |

2. A mixture of a pigment of the formula (1) as claimed in claim 1, comprising at least 25% of phase II, phase IV, phase V, phase VI or a mixture of two, three or four of these phases.

3. A mixture of a pigment of the formula (1) as claimed in claim 1, comprising at least 50% of phase II, phase IV, phase V, phase VI or a mixture of two, three or four of these phases.

4. A mixture of a pigment of the formula (1) as claimed in claim 1, comprising at least 75% of phase II, phase IV, phase V, phase VI or a mixture of two, three or four of these phases.

5. A mixture of a pigment of the formula (1) as claimed in claim 1, comprising at least 90% of phase II, phase IV, phase V, phase VI or a mixture of two, three or four of these phases.

6. A mixture of a pigment of the formula (1) as claimed in claim 1, comprising at least 10% of phase II phase IV, phase V, phase VI or a mixture of two, three or four of these phases.

7. A pigmented composition comprising a pigment of the formula (1) as claimed in claim 1, wherein the composition is selected from the group consisting of coating materials, plastics, printing inks, aqueous or solvent-based pigment preparations, cosmetics, electrophotographic toners, electrophotographic developers, powder coating materials, inks, ink jet inks, color filters, seed , and pulp for dyeing paper.

8. A method for pigmenting a composition comprising the step of adding a pigment of the formula (1) as claimed in claim 1 to the compound, wherein the compound is selected from the group consisting of costing materials, plastics, printing inks, aqueous or solvent-based pigment preparations, cosmetics, electrophotographic toners and developers, powder coating materials, inks, inkjet inks, color filters, seeds, and paper.

9. A process for phase conversion of a compound of the formula (1)

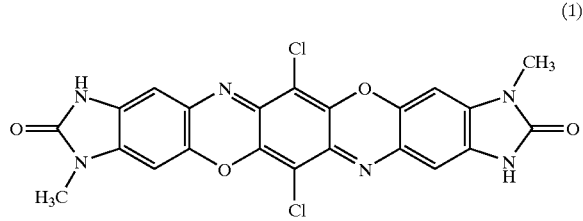

(1)

or of a tautomer thereof, which comprises causing to act on the compound of the formula (1) an organic solvent selected from the group consisting of N-methyipyrrolidone, $C_1$–$C_{20}$-alcohol, 1,2,4-trichlorobenzene, trifluoroacetic acid, and dichloroacetic acid, or a mixture of said solvents, or a mixture of 1,2-dichlorobenzene and trifluoroacetic acid, at a temperature of between 0 and 250° C.

10. The process as claimed in claim 9, wherein phase conversion takes place at a temperature of between 20 and 210° C.

11. The process as claimed in claim 9, wherein the compound of the formula (1) is dissolved in trifluoroacetic acid and then precipitated using acetic acid.

12. The process as claimed in claim 9, wherein the compound of the formula (1) is dissolved in trifluoroacetic acid or in a mixture of trifluoroacetic acid and o-dichlorobenzene and then precipitated by evaporating the trifluoroacetic acid.

13. The process as claimed in claim 9, wherein the compound of the formula (1) is heated to boiling in N-methyl pyrrolidone.

* * * * *